(12) United States Patent
Hall et al.

(10) Patent No.: US 9,060,519 B2
(45) Date of Patent: Jun. 23, 2015

(54) INSECTICIDALLY ACTIVE PYRIDYL-THIAZOLE AND PYRIDYL-THIADIAZOLE DERIVATIVES

(75) Inventors: Roger Graham Hall, Stein (CH); Andrew Edmunds, Stein (CH); André Jeanguenat, Stein (CH); Thomas Pitterna, Stein (CH); Sebastian Rendler, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/118,923

(22) PCT Filed: Jun. 27, 2012

(86) PCT No.: PCT/EP2012/062405
§ 371 (c)(1),
(2), (4) Date: Nov. 20, 2013

(87) PCT Pub. No.: WO2013/000931
PCT Pub. Date: Jan. 3, 2013

(65) Prior Publication Data
US 2014/0283218 A1     Sep. 18, 2014

(30) Foreign Application Priority Data
Jun. 29, 2011   (EP) .................................. 11171950

(51) Int. Cl.
| C07D 417/04 | (2006.01) |
| C07D 417/14 | (2006.01) |
| A01N 43/78 | (2006.01) |
| A01N 43/90 | (2006.01) |

(52) U.S. Cl.
CPC .............. *A01N 43/90* (2013.01); *C07D 417/04* (2013.01); *C07D 417/14* (2013.01); *A01N 43/78* (2013.01)

(58) Field of Classification Search
CPC ..... A01N 43/78; A01N 43/90; C07D 417/04; C07D 417/14
USPC ............ 424/405, 489; 514/183, 247, 252.01, 514/252.03, 252.05, 252.06, 256, 266.1, 514/266.22, 266.3, 269, 274, 277, 317, 319, 514/322, 323, 326, 331, 339, 342, 363, 514/365; 544/224, 238, 239, 240, 242, 256, 544/263, 283, 284, 298, 316, 317, 322, 331, 544/332, 334, 335; 546/192, 199, 206, 209, 546/210, 268.7, 270.4, 329, 334; 548/136, 548/146, 202, 203, 205; 504/100
See application file for complete search history.

(56) References Cited

U.S. PATENT DOCUMENTS

2010/0292253 A1 * 11/2010 Trullinger et al. ............. 514/256
2011/0034445 A1 *  2/2011 Beier et al. .................. 514/224.2
2011/0263603 A1 * 10/2011 Koerber et al. ............ 514/236.8

FOREIGN PATENT DOCUMENTS

WO        2009/149858 A1    12/2009
WO    WO2009/149858 A1 * 12/2009 ........... C07D 401/04

OTHER PUBLICATIONS

International Search Report for International Patent Application No. PCT/EP2012/062405, Jul. 26, 2012.

* cited by examiner

*Primary Examiner* — Jane C Oswecki
(74) *Attorney, Agent, or Firm* — Brian D. McAlhaney

(57) ABSTRACT

Compounds of formula I

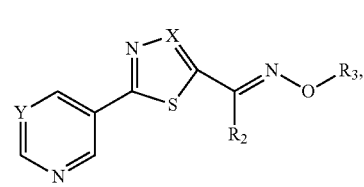

wherein the substituents are as defined in claim 1, and the agrochemically acceptable salts and all stereoisomers and tautomeric forms of the compounds of formula I can be used as insecticides and can be prepared in a manner known per se.

15 Claims, No Drawings

INSECTICIDALLY ACTIVE PYRIDYL-THIAZOLE AND PYRIDYL-THIADIAZOLE DERIVATIVES

The present invention relates to insecticidally active 2-(3-pyridyl)-thiazole and 2-(3-pyridyl)-thiadiazole derivatives, to processes for their preparation, to compositions comprising those compounds, and to their use for controlling insects or representatives of the order Acarina.

2-(3-Pyridyl)-thiazole derivatives with insecticidal action are known and described, for example, in U.S. Pat. No. 4,080,457, WO 2009/149858, WO 2010/129497 and WO 2010/006713.

There have now been found novel 2-(3-pyridyl)-thiazole and 2-(3-pyridyl)-thiadiazole derivatives derivatives with pesticidal properties.

The present invention accordingly relates to compounds of formula I

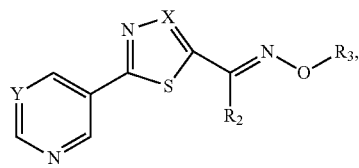

(I)

wherein
X is nitrogen or C—$R_1$;
Y is nitrogen or C—$R_4$;
$R_1$ is hydrogen, $C_1$-$C_6$alkyl or halogen;
$R_2$ is $C_1$-$C_6$alkyl which can be mono- to polysubstituted by substituents independently selected from the group consisting of halogen, nitro, cyano, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or
$R_2$ is $C_3$-$C_6$cycloalkyl which can be mono- to polysubstituted by substituents independently selected from the group consisting of halogen, nitro, cyano, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl;
$R_3$ is a five- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the five- to ten-membered ring system itself to be mono- to polysubstituted by substituents independently selected from the group consisting of halogen, cyano, nitro, amino, hydroxy, $C_1$-$C_6$alkyl, $C_2$-$C_6$alkenyl, $C_2$-$C_6$alkynyl, $C_2$-$C_6$alkynyloxy, $C_3$-$C_6$cycloalkyl, $C_5$-$C_7$cycloalkenyl, $C_5$-$C_8$cycloalkynyl, $C_3$-$C_6$cycloalkylamino, $C_1$-$C_6$haloalkyl, $C_2$-$C_6$haloalkenyl, $C_2$-$C_6$haloalkynyl, $C_3$-$C_6$halocycloalkyl, $C_2$-$C_7$halocycloalkenyl, $C_2$-$C_8$halocycloalkynyl, $C_1$-$C_6$alkoxy-$C_1$-$C_6$alkylamino, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$alkylamino, di-($C_1$-$C_6$alkyl)amino, $C_3$-$C_6$cycloalkylamino, $C_1$-$C_6$alkyl-$C_3$-$C_6$cycloalkylamino, $C_1$-$C_6$alkylcarbonyl, $C_1$-$C_6$alkoxycarbonyl, $C_1$-$C_6$alkylaminocarbonyl, $C_1$-$C_6$dialkylaminocarbonyl, $C_1$-$C_6$alkoxycarbonyloxy, $C_1$-$C_6$alkylaminocarbonyloxy, $C_1$-$C_6$dialkylaminocarbonyloxy, tri-($C_1$-$C_6$alkyl)silyl or phenyl, it being possible for the phenyl group in turn to be mono- to polysubstituted by substituents independently selected from the group consisting of hydroxy, $C_1$-$C_6$alkyl, $C_1$-$C_6$haloalkyl, $C_1$-$C_6$alkoxy, $C_1$-$C_6$alkylthio, $C_1$-$C_6$haloalkylthio, $C_2$-$C_6$alkenylthio, $C_2$-$C_6$haloalkenylthio, $C_2$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di-($C_1$-$C_2$alkyl)aminosulfonyl, di($C_1$-$C_4$alkyl)amino, halogen, cyano and nitro; and the substituents at the nitrogen atoms in the ring systems being other than halogen; and
$R_4$ is hydrogen or halogen;
and agrochemically acceptable salts, enantiomers, tautomers and N-oxides of those compounds.

Compounds of formula I which have at least one basic centre can form, for example, acid addition salts, for example with strong inorganic acids such as mineral acids, for example perchloric acid, sulphuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluene-sulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulphinyl is, for example, methylsulphinyl, ethylsulphinyl, propylsulphinyl, isopropylsulphinyl, n-butylsulphinyl, isobutylsulphinyl, sec-butylsulphinyl, tert-butylsulphinyl; preferably methylsulphinyl and ethylsulphinyl.

Alkylsulphonyl is, for example, methylsulphonyl, ethylsulphonyl, propylsulphonyl, isopropylsulphonyl, n-butylsulphonyl, isobutylsulphonyl, sec-butylsulphonyl or tert-butylsulphonyl; preferably methylsulphonyl or ethylsulphonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of the present invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

According to the present invention, a five- to ten-membered monocyclic or fused bicyclic ring system which may be aromatic, partially saturated or fully saturated is, depending of the number of ring members, for example, selected from the group consisting of

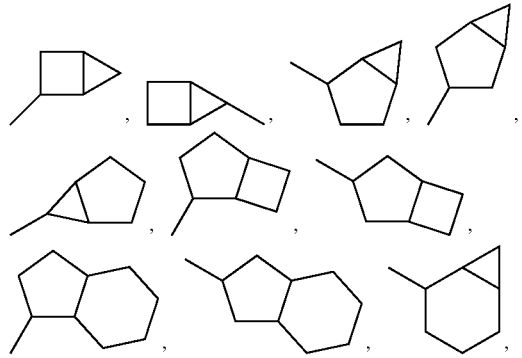

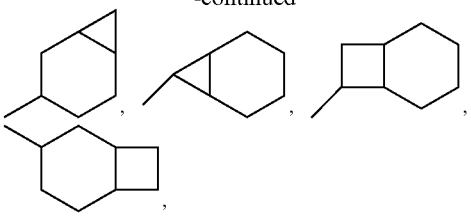

cyclopentyl, cyclohexyl, where said cycloalkyl groups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

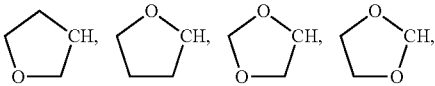

-continued

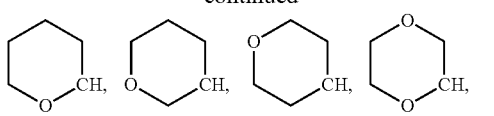
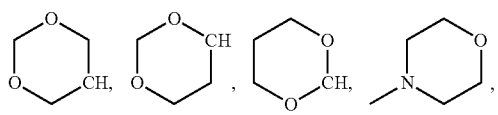
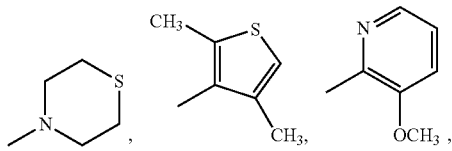
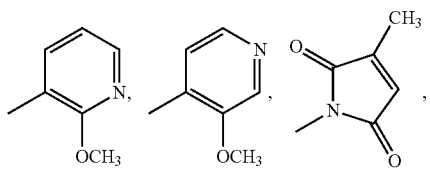
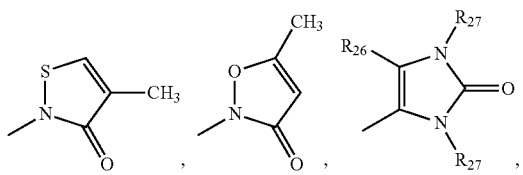
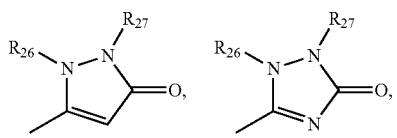
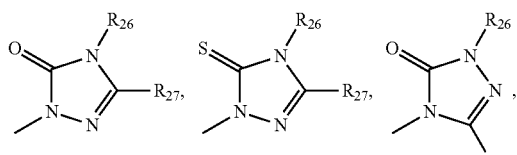
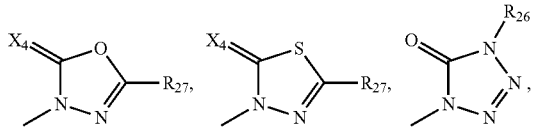
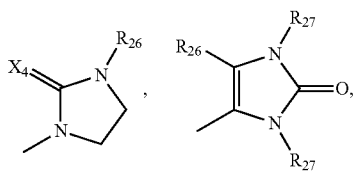
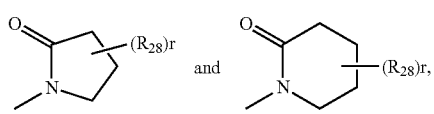

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions, for example as in

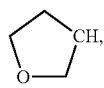

the linkage site is located at the carbon atom labelled "CH" or in a case such as, for example,

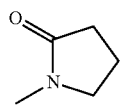

at the bonding site indicated at the bottom left.

Preferred compounds of formula I are those, wherein $R_2$ is $C_1$-$C_6$alkyl which can be mono- to polysubstituted by substituents independently selected from the group consisting of halogen, nitro, cyano, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl.

In preferred compounds of formula I, said ring system $R_3$ is aromatic. Preferably said aromatic ring system $R_3$ is mono- to polysubstituted by substituents selected from the group consisting of $C_1$-$C_6$alkyl, $C_1$-$C_6$haloalkyl, $C_1$-$C_6$alkylthio, $C_1$-$C_6$alkoxy, $C_1$-$C_6$alkoxy-$C_1$-$C_6$alkylamino, $C_1$-$C_6$alkoxycarbonyl, $C_2$-$C_6$alkynyloxy, $C_3$-$C_6$cycloalkyl, halogen, cyano, nitro, amino, di-($C_1$-$C_6$alkyl)amino, $C_3$-$C_6$cycloalkylamino and phenyl, it being possible for the phenyl group in turn to be mono- to polysubstituted by substituents independently selected from the group consisting of halogen and $C_1$-$C_6$alkoxy. In particular said aromatic ring system $R_3$ is selected from the group consisting of [1,2,4]triazolo[4,3-b]pyridazinyl, pyridazinyl, pyridyl, pyrimidinyl and quinazolinyl. Especially preferred said aromatic ring system is six-membered and contains 2 nitrogen atoms. Most preferred said aromatic ring system is 2-pyrimidyl. In all of the preferences mentioned above, X is preferably C—$R_1$, wherein $R_1$ is preferably $C_1$-$C_4$alkyl, in particular methyl. In all of the preferences mentioned above, Y is preferably C—$R_4$, wherein $R_4$ is preferably hydrogen.

An outstanding group of compounds of formula I is represented by the compounds of formula I, wherein said ring system $R_3$ is aromatic with the preferences mentioned above, and $R_2$ is $C_1$-$C_6$alkyl which can be mono- to polysubstituted by substituents independently selected from the group consisting of halogen, nitro, cyano, $C_1$-$C_6$alkoxy, $C_1$-$C_6$alkylthio, $C_1$-$C_6$alkylsulfinyl and $C_1$-$C_6$alkylsulfonyl. In said outstanding group, $R_4$ is in particular hydrogen or fluorine. In said outstanding group X is preferably C—R$_1$, wherein R$_1$ is preferably C$_1$-C$_4$alkyl, in particular methyl. In said outstanding group, Y is preferably C—R$_4$, wherein R$_4$ is preferably hydrogen.

A further outstanding group of compounds of formula I is represented by the compounds of formula I, wherein said ring system R$_3$ is aromatic with the preferences mentioned above, and R$_1$ is C$_1$-C$_6$alkyl or halogen; and R$_2$ is C$_1$-C$_6$alkyl. In said further outstanding group R$_4$ is in particular hydrogen or fluorine. In said further outstanding group, X is preferably C—R$_1$, wherein R$_1$ is preferably C$_1$-C$_4$alkyl, in particular methyl. In said further outstanding group, Y is preferably C—R$_4$, wherein R$_4$ is preferably hydrogen.

Another outstanding group of compounds of formula I is represented by the compounds of formula I, wherein said ring system R$_3$ is aromatic with the preferences mentioned above, and R$_1$ is methyl or chloro; and R$_2$ is methyl. In said another outstanding group R$_4$ is in particular hydrogen or fluorine. In said another outstanding group, X is preferably C—R$_1$, wherein R$_1$ is preferably C$_1$-C$_4$alkyl, in particular methyl. In said another outstanding group, Y is preferably C—R$_4$, wherein R$_4$ is preferably hydrogen.

In a further preferred group of compounds of formula I, R$_2$ is C$_1$-C$_6$alkyl which can be mono- to disubstituted by substituents independently selected from the group consisting of halogen, nitro, cyano, C$_1$-C$_6$alkoxy, C$_1$-C$_6$alkylthio, C$_1$-C$_6$alkylsulfinyl and C$_1$-C$_6$alkylsulfonyl. In said further preferred group R$_4$ is in particular hydrogen or fluorine. In said further preferred group, X is preferably C—R$_1$, wherein R$_1$ is preferably C$_1$-C$_4$alkyl, in particular methyl. In said further preferred group, Y is preferably C—R$_4$, wherein R$_4$ is preferably hydrogen.

In a particular preferred group of compounds of formula I, R$_1$ is C$_1$-C$_6$alkyl or halogen; and R$_2$ is C$_1$-C$_6$alkyl. In said particular preferred group R$_4$ is in particular hydrogen or fluorine. In said particular preferred group, X is preferably C—R$_1$, wherein R$_1$ is preferably C$_1$-C$_4$alkyl, in particular methyl. In said particular preferred group, Y is preferably C—R$_4$, wherein R$_4$ is preferably hydrogen.

In an especially preferred group of compounds of formula I,
R$_1$ is methyl or chloro; and R$_2$ is methyl. In said especially preferred group R$_4$ is in particular hydrogen or fluorine. In said especially preferred group, X is preferably C—R$_1$, wherein R$_1$ is preferably C$_1$-C$_4$alkyl, in particular methyl. In said especially preferred group, Y is preferably C—R$_4$, wherein R$_4$ is preferably hydrogen.

Further compounds of formula I are preferred, wherein R$_4$ is hydrogen or fluorine.

In an especially preferred embodiment of the invention, the substituents of the formula I have the following meanings:
X is oxygen or C—R$_1$,
R$_1$ is hydrogen, C$_1$-C$_6$alkyl or halogen;
Y is —C—H;
R$_2$ is C$_1$-C$_6$alkyl which can be substituted by halogen; or R$_2$ is C$_3$-C$_6$cycloalkyl;
R$_3$ is a ring system selected from the group consisting of [1,2,4]triazolo[4,3-b]pyridazinyl, pyridazinyl, pyridyl, pyrimidinyl, triazinyl and quinazolinyl; said ring system can be mono-, di- or trisubstituted by substituents selected from the group consisting of C$_1$-C$_6$alkyl, C$_1$-C$_6$haloalkyl, C$_1$-C$_6$haloalkoxy, C$_1$-C$_6$alkylthio, C$_1$-C$_6$alkoxycarbonyl, C$_1$-C$_6$alkoxy-C$_1$-C$_6$alkyl, di-(C$_1$-C$_6$alkyl)amino, C$_3$-C$_6$cycloalkylamino, C$_3$-C$_6$cycloalkyl, C$_2$-C$_6$alkynyloxy, C$_1$-C$_6$alkoxy, halogen, cyano, nitro, amino, pyridyl, wherein said pyridyl can be substituted by C$_1$-C$_6$alkoxy-C$_1$-C$_6$alkylamino, and by phenyl, wherein said phenyl can be mono- to polysubstituted by substituents independently selected from the group consisting of halogen and C$_1$-C$_6$alkoxy.

The method according to the invention for the preparation of compounds of formula (I)

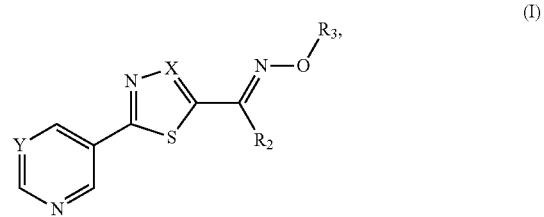

wherein X, Y, R$_2$, and R$_3$ are as described as in formula (I) above, comprises reacting a compound of formula (II)

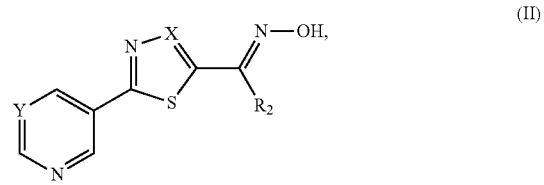

with a compound of formula (III)

wherein R$_3$ is as described as in formula (I) above, and LG represents a leaving group, for example halogen, in the presence of a base, and optionally in the presence of a catalyst for example dimethylaminopyridine (DMAP).

Alternatively, compounds of the formula (I) can be prepared by reacting compounds of the formula (IV)

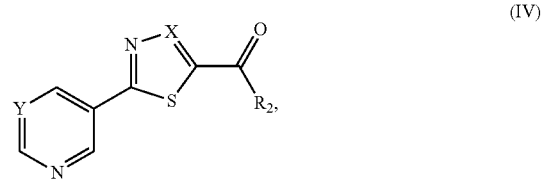

wherein R$_2$ is as described as in formula I above, with a compound of formula (V)

wherein R$_3$ is as described as in formula (I) above, under conditions where water is removed from the reaction mixture.

The compounds of formula (II) and (IV) may be prepared according to reaction scheme 1:

Reaction Scheme 1:

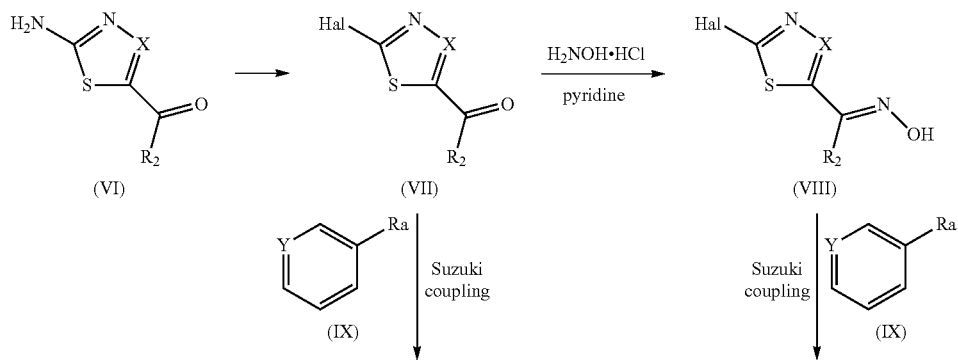

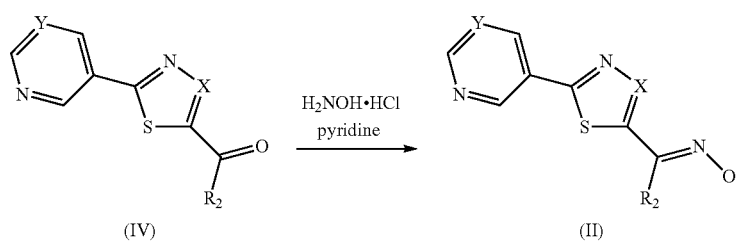

Compound of formula (VI) are either known or may be prepared by methods well described in the literature. Compounds of formula (VI) are converted to compounds of formula (VII) under conditions used for the Sandmeyer reaction. The compound of formula (VII) is coupled in a Suzuki reaction with a boronic derivative of formula (IX) wherein Ra is $B(OH)_2$, $B(OMe)_2$, $B(OiPr)_2$, $BF_3K$ or B(—OCMe$_2$CMe2O—) to compound of formula (IV). Alternatively compound of formula (VII) is converted to compound of formula (VIII) using hydroxylamine with removal of water and this compound of formula (VIII) is coupled in a Suzuki reaction with a boronic derivative of formula (IX) with Ra as defined above to compound of formula (II). Compound of the formula (IV) are converted to compounds of formula (II) by reaction with hydroxylamine and removal of water. The Suzuki reaction is known from the literature e.g. J. P. Wolfe, J. S. Nakhla, The Suzuki Reaction in Name Reactions for Homologations, John Wiley & Sons, Inc., Hoboken, N. J., 2009, Pt. 1, 163.

Compounds of formula (III) are either known or can be prepared by known methods. Compounds of formula (V) are either known or can be prepared by known methods. Compounds of formula (IVA), where X represents $CR_1$, may be prepared according to reaction scheme 2:

Reaction scheme 2:

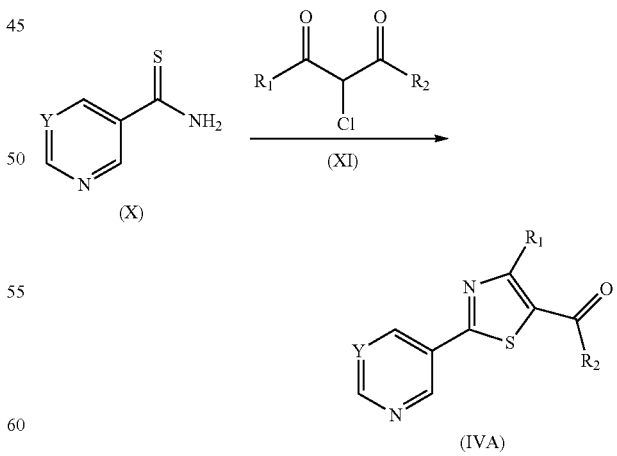

Compounds of formula (X) are coupled with compounds of formula (XI) to give compounds of formula (IVA). Conditions for this process are reported in Bioorganic & Medicinal Chemistry Letters, 17(4), 1056-1061; 2007. Compounds of formula (X) are known or maybe prepared by methods well known in the literature. Compounds of formula (XI) are known or may be prepared by methods well known in the literature.

A further synthesis of compounds of formula I is illustrated in scheme 3.

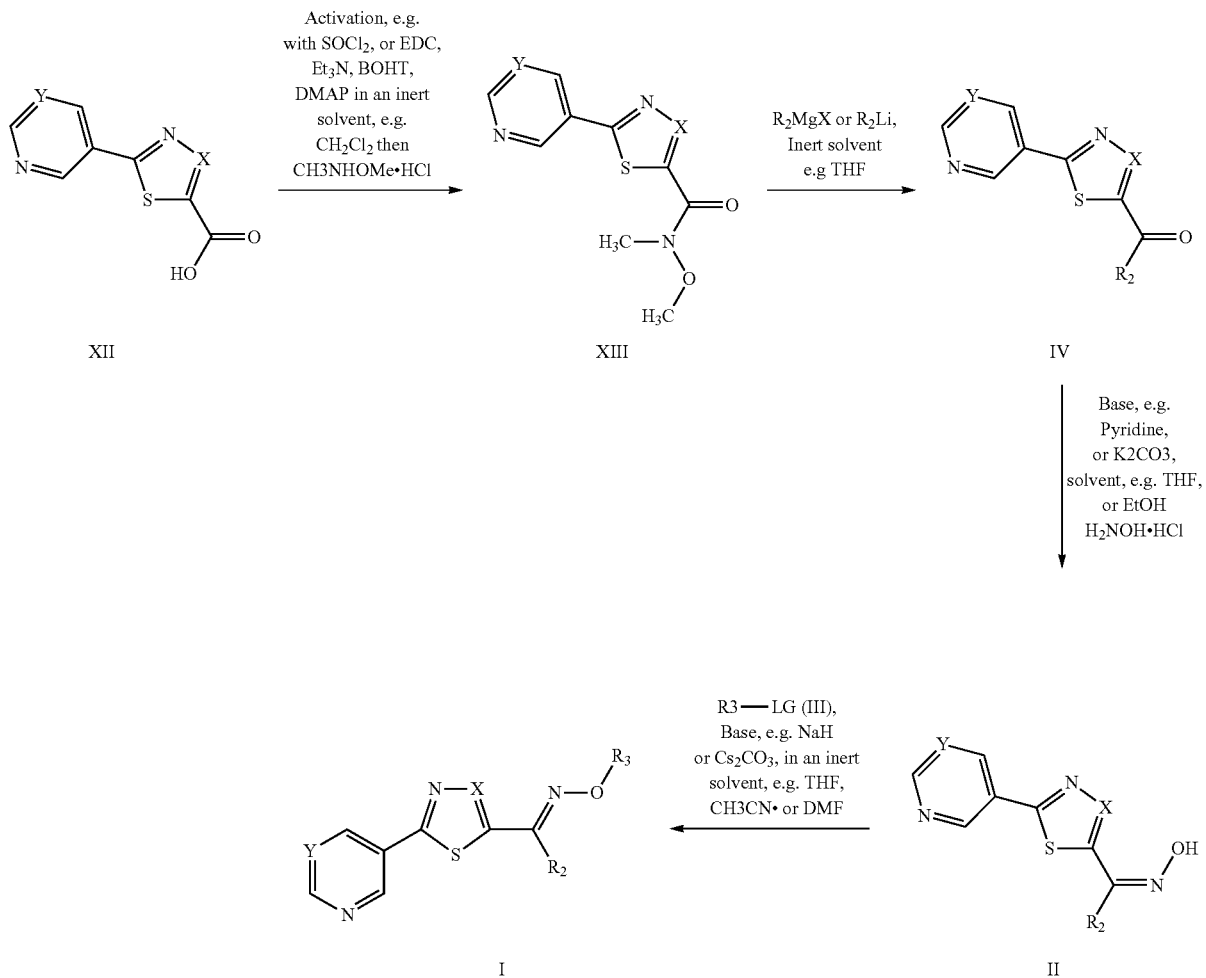

In scheme 3, compounds of formula XII (prepared according to WO09149858 and WO10006713) are activated at the hydroxyl position, e.g. with thionyl chloride or for example 1-ethyl-3-(3-dimethylaminopropyl)carbodiimide (EDC) or dicyclohexylcarbodiimide (DCC) in the presence of a base, for example triethylamine or dimethyl amino pyridine (DMAP) in a solvent, such as dichloromethane, at temperatures between 0° C. and 50° C., preferably 0° C. and 20° C., to give compounds of formula XIII. Compounds of formula XIII can be reacted with an alkylmetal compound, for example an alkylmagnesium Grignard of the formula $R_2MgX$ (where X is halogen) or an alkyllithium reagent of the formula $R_2Li$, wherein $R_2$ is as previously defined, in an inert solvent such as THF at temperatures between preferably −78° C. and 20° C., to give compounds of formula IV. Such Weinreb amide chemistry is well known to those skilled in the art (see for example WO10006713). Compounds of formula IV are converted to compounds of formula I by methods previously described, or those shown in scheme 3.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetrany-* chus spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremmus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp., *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., Scarabeidae, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example, *Ceratophyllus* spp., *Ctenocephalides* spp. and *Xenopsylla cheopis*;

from the order Thysanoptera, for example, *Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice). The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type. In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances. In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-me-thylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno-xypolyethoxyethanol, polyethylene glycol or octylphenoxypolyethoxyethanol. Also suitable are fatty acid esters of polyoxyethylene sorbitan, such as polyoxyethylene sorbitan trioleate. The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 20%
surfactant: 1 to 30%, preferably 10 to 20%
solvent: 5 to 98%, preferably 70 to 85%

Dusts:
active ingredient: 0.1 to 10%, preferably 0.1 to 1%
solid carrier: 99.9 to 90%, preferably 99.9 to 99%

Suspension Concentrates:
active ingredient: 5 to 75%, preferably 10 to 50%
water: 94 to 24%, preferably 88 to 30%
surfactant: 1 to 40%, preferably 2 to 30%

Wettable Powders:
active ingredient: 0.5 to 90%, preferably 1 to 80%
surfactant: 0.5 to 20%, preferably 1 to 15%
solid carrier: 5 to 99%, preferably 15 to 98%

Granulates:

active ingredient: 0.5 to 30%, preferably 3 to 15%
solid carrier: 99.5 to 70%, preferably 97 to 85%

PREPARATORY EXAMPLES

Example 1

Preparation of 1-[5-(3-pyridyl)-1,3,4-thiadiazol-2-yl]-N-pyrimidin-2-yloxy-ethanimine (Compound 1.040)

(Compound No. 1.040)

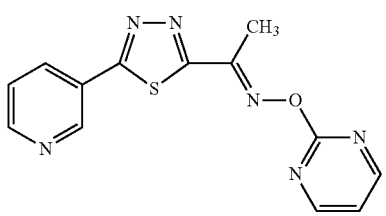

Step a: Preparation of 1-[5-(3-pyridyl)-1,3,4-thiadiazol-2-yl]ethanone oxime

A suspension of 1-[5-(3-pyridyl)-1,3,4-thiadiazol-2-yl]ethanone (1.0 g, 4.68 mmol, prepared according to WO 2010/006713) in 50 ml EtOH was treated with hydroxylamine hydrochloride (0.345 g, 4.91 mmol) and potassium carbonate (0.686 g, 4.91 mmol), and stirred at room temperature, monitored by LCMS and TLC. After 3 hours, the mixture was concentrated in vacuo to approximately 10 ml. Addition of saturated ammonium chloride gave a precipitate which was filtered, and washed successively with water, isopropanol, and tertiary-butyl methyl ether. This yielded 1-[5-(3-pyridyl)-1,3,4-thiadiazol-2-yl]ethanone oxime (577 mg, 51%) as a 5:1 mixture of isomers.

LCMS: 220 (M+1).

$^1$H-NMR (in d$_6$-DMSO): Major isomer: 13.0 (br s, 1H); 9.21 (s, 1H); 8.78 (d, 1H); 8.50 (d, 1H); 7.61 (dd, 1H); 2.51 ppm (s, 3H); Minor isomer: 12.4 13.0 (br s, 1H); 9.20 (s, 1H); 8.78 (d, 1H); 8.40 (d, 1H); 7.61 (dd, 1H); 2.31 ppm (s, 3H).

Step b

A solution of 1-[5-(3-pyridyl)-1,3,4-thiadiazol-2-yl]ethanone oxime (0.1 g, 0.436 mmol) in acetonitrile (5 ml) was stirred at ambient temperature and treated with cesium carbonate (0.43 g, 1.31 mmol) and 2-chloropyrimidine (0.079 g, 0.654 mmol). The reaction mixture was allowed to stir at ambient temperature and monitored by TLC and LC/MS. After 2 days, the mixture was concentrated in vacuo. The residue was stirred with ethyl acetate, filtered and the ethyl acetate concentrated in vacuo. Purification by recrystallisation gave a single isomer of 1-[5-(3-pyridyl)-1,3,4-thiadiazol-2-yl]-N-pyrimidin-2-yloxy-ethanimine (70 mg, 23%) in form of beige crystals.

LCMS: 299 (M+1).

$^1$H-NMR (in d$_4$-MeOD): 9.29 (s, 1H); 8.76 (d, 2H); 8.55 (d, 1H); 8.50 (d, 1H); 7.66 (dd, 1H); 7.39 (t, 1H): 2.79 ppm (s, 3H).

Example 2

Preparation of 1-[2-(3-pyridyl)thiazol-5-yl]-N-pyrimidin-2-yloxy-ethanimine (Compound No. 1.041)

(Compound No. 1.041A and 1.041B)

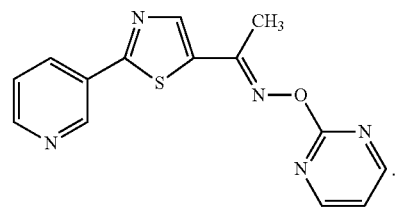

Step a: Preparation of N-methoxy-N-methyl-2-(3-pyridyl)thiazole-5-carboxamide

A suspension of 2-(3-pyridyl)thiazole-5-carbonyl chloride (4.6 g, 19.5 mmol) prepared according to WO 2009/149858) in methylene chloride (100 ml) was cooled to 0° C. and treated with triethyl amine (6.03 g, 58.4 mmol), dimethylamino pyridine (12 mg, 0.097 mmol) and then N-methoxymethanamine hydrochloride (2.9 g, 29.2 mmol). The mixture was allowed to warm up to ambient temperature and monitored by TLC and LC/MS. After completion, the reaction mixture was diluted with methylene chloride, washed with water, dried over magnesium sulfate, and the solvent removed by concentration in vacuo, to give 3.99 g (82%) of N-methoxy-N-methyl-2-(3-pyridyl)thiazole-5-carboxamide as a pale solid.

LCMS: 250 (M+1).

$^1$H-NMR (in CDCl3): 9.24 (s, 1H); 8.72 (d, 1H); 8.64 (s, 1H); 8.35 (d, 1H); 7.46 (dd, 1H); 3.83 (s, 3H); 3.42 ppm (s, 3H).

Step b. Preparation of 1-[2-(3-pyridyl)thiazol-5-yl]ethanone

A solution of N-methoxy-N-methyl-2-(3-pyridyl)thiazole-5-carboxamide (5.6 g, 21.9 mmol) in 150 ml of THF was cooled to 0° C. and treated with methyl magnesium bromide (8.4 ml of a 3M solution in diethyl ether, 24.1 mmol). The reaction was stirred at 0° C. and shown to be complete by LC/MS and TLC after 1 Hr. The mixture was hydrolyzed with 5 ml water and evaporated. The residue was taken up in 200 ml of ethyl acetate and washed with 2×80 ml water and 1×80 ml brine. The organic phase were dried over Na$_2$SO$_4$, filtrated and concentrated in vacuo to give the title compound (4.4 g, 98%) as orange crystals which were pure enough for the next step without further purification.

LCMS: 206 (M+1).

$^1$H-NMR (in CDCl3): 9.124 (s, 1H); 8.80 (d, 1H); 8.39 (d, 1H); 7.51 (dd, 1H); 2.87 ppm (s, 3H).

Step c. Preparation of 1-[2-(3-pyridyl)thiazol-5-yl]ethanone oxime

A suspension of 1-[2-(3-pyridyl)thiazol-5-yl]ethanone (0.8 g, 3.76 mmol) in 50 ml EtOH was treated with hydroxylamine hydrochloride (0.277 g, 3.95 mmol) and potassium carbonate (0.551 g, 3.95 mmol), and stirred at ambient temperature, monitored by LCMS and TLC, which indicated a ca. 1:1 mixture of isomer formation. After 3 hours, the mixture was concentrated in vacuo to approximately 10 ml. Addition of saturated ammonium chloride gave Isomer A of the title product as a beige precipitate which was filtered, and washed successively with water, isopropanol, and tertiary-butyl methyl ether (yield 156 mg).

LCMS: 220 (M+1).

$^1$H-NMR (in $d_6$-DMSO): Isomer A: 11.58 (br s, 1H); 9.12 (s, 1H); 8.68 (d, 1H); 8.31 (d, 1H); 8.20 (s, 1H); 7.55 (dd, 1H); 2.22 ppm (s, 3H).

The filtrate from above was extracted with ethyl acetate, and the combined organic phases washed with brine, dried over $Na_2SO_4$, filtered and concentrated in vacuo to give 621 mg of a beige solid which was principally isomer B.

LCMS: 220 (M+1).

$^1$H-NMR (in $d_6$-DMSO): Isomer B: 12.12 (br s, 1H); 9.20 (s, 1H); 8.69 (d, 1H); 8.40 (s, 1H); 8.39 (d, 1H); 7.55 (dd, 1H); 2.31 ppm (s, 3H).

Step d (Isomer A)

A suspension of 1-[2-(3-pyridyl)thiazol-5-yl]ethanone oxime (isomer A, 0.15 g, 0.657 mmol) in acetonitrile (5 ml) was stirred at ambient temperature and treated with carbonate (0.648 g, 1.97 mmol) and 2-chloropyrimidine (0.119 g, 0.985 mmol) and allowed to stir at ambient temperature. After 2 days (80% conversion), the reaction mixture was concentrated in vacuo and the residue was stirred with ethyl acetate, filtered and the ethyl acetate concentrated in vacuo. Purification by flash chromatography eluting with ethyl acetate gave 1-[2-(3-pyridyl)thiazol-5-yl]-N-pyrimidin-2-yloxy-ethanimine (0.074 g, 38%) as a single isomer as slightly yellow crystals.

LCMS: 298 (M+1).

$^1$H-NMR (in CDCl3): 9.30 (s, 1H); 8.71 (d, 2H); 8.39 (s, 1H); 8.35 (d, 1H); 7.42 (dd, 1H); 7.15 (t, 1H): 2.68 ppm (s, 3H).

Step d (Isomer B)

A suspension of 1-[2-(3-pyridyl)thiazol-5-yl]ethanone oxime (76 mg, 0.33 mmol) and cesium carbonate (330 mg, 1.0 mmol) in acetonitrile (10 ml) was stirred at ambient temperature and treated with 2-chlopyrimidine (60 mg, 0.5 mmol). The reaction was monitored by TLC and LC/MS until ca. 70% completion, and then concentrated in vacuo. The solid residue was stirred with ethyl acetate, filtered and concentrated in vacuo. The crude product was purified by flash chromatography, eluting with ethyl acetate:MeOH (95:5), to give isomer B of 1-[2-(3-pyridyl)thiazol-5-yl]-N-pyrimidin-2-yloxy-ethanimine (46 mg, 46%) as white crystals.

LCMS: 298 (M+1).

$^1$H-NMR (in CDCl3): 9.23 (s, 1H); 8.71 (m, 3H); 8.30 (d, 1H); 8.18 (s, 1H); 7.44 (dd, 1H); 7.13 (t, 1H): 2.64 ppm (s, 3H).

Example 3

Preparation of 1-(4-methyl-2-pyridin-3-yl-thiazol-5-yl)-ethanone O-(5-chloro-pyrimidin-2-yl)-oxime (Compound No. 1.017)

(Compound No. 1.017)

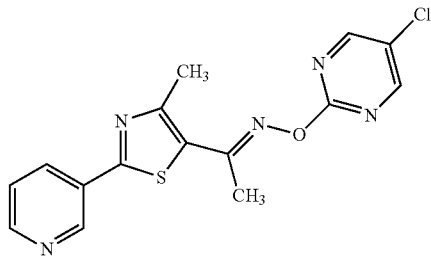

Step a: Preparation of 2-bromo-4-methyl-5-acetylthiazole

2-Amino-4-methyl-5-acetylthiazole (0.5 g, 3.2 mmol) was suspended in acetonitrile (14 ml) and stirred at ambient temperature. Copper II bromide (0.715 g, 3.2 mmol) was added, followed by isopentylnitrite (1.125 g, 9.6 mmol). The reaction mixture was heated to 60° C. for a period of 3.5 hours. After cooling to ambient temperature, the solvent was removed by evaporation, and the crude material was purified by column chromatography using heptane: ethyl acetate (4:1) as eluent. The product was obtained as a light yellow oil. $^1$H NMR (CDCl3): 2.5 ppm (3H, s); 2.7 ppm (3H, s).

Step b: Preparation of 2-(pyridin-3-yl)-4-methyl-5-acetylthiazole

2-Bromo-4-methyl-5-acetylthiazole (12.0 g, 54.5 mmol) was dissolved in a mixture of dimethoxyethane (180 ml), water (76 ml) and ethanol (52 ml). To this solution was then added 3-pyridineboronic acid (20.1 g, 163.5 mmol), tetrakis(PPh$_3$)palladium(0) (6.3 g, 5.4 mmol), and sodium carbonate (17.3 g, 163.5 mmol), and the reaction mixture was heated to 160° C. in a microwave oven for a period of 1 hour. The reaction was allowed to cool to ambient temperature, the solvents were removed by evaporation, the residue taken up in ethyl acetate, and the mixture filtered through silica gel and celite. The ethyl acetate was washed with water, dried over magnesium sulfate, and the solvent removed by evaporation. The crude product was purified by chromatograph and the product was obtained as a fawn colored solid. $^1$H NMR (CDCl3): 2.6 ppm (3H, s); 2.8 ppm (3H, s); 7.4 ppm (1H, m); 8.25 ppm (1H, m); 8.7 ppm (1H, m); 9.2 ppm (1H, m).

Step c: Preparation of 2-(Pyridin-3-yl)-4-methyl-5-ethanoneoximethiazole 2-(Pyridin-3-yl)-4-methyl-5-acetylthiazole (7.86 g, 36 mmol) was dissolved in pyridine (150 ml) and stirred at ambient temperature. Hydroxylamine hydrochloride (25.0 g, 360 mmol) was added and the reaction mixture heated to 120° C. for 20 hours. The reaction mixture was allowed to cool to ambient temperature, and the solvent removed by evaporation. The residue was then stirred with water, filtered and the solid dried under vacuum. The residue was further purified by heating with isopropanol (70 ml), cooling and then filtering the solid. The product was obtained as a fawn colored solid. $^1$H NMR (CDCl3): 2.4 ppm (3H, s); 2.7 ppm (3H, s); 7.45 ppm (1H, m); 8.4 ppm (1H, m); 8.6 ppm (1H, m); 9.3 ppm (1H, m); 11.3 (1H, br.s).

Step d: Preparation of 1-(4-methyl-2-pyridin-3-yl-thiazol-5-yl)-ethanone O-(5-chloro-pyrimidin-2-yl)-oxime (Compound 1.017)

2-(Pyridin-3-yl)-4-methyl-5-ethanoneoximethiazole (0.06 g, 0.26 mmol) was dissolved in dimethylformamide (2.0 ml). To this solution was added sodium hydride (0.012 g, 0.28 mmol, 60% solution in oil) at 10° C. and the reaction was stirred at ambient temperature for 20 minutes. After cooling to 10° C., 2,5-dichloropyrimidine (0.058 g, 0.39 mmol) was added and the reaction was stirred at ambient temperature for 15 hours. The reaction mixture was poured onto ice water, and the solid isolated by filtration. The solid was further purified by stirring with toluene and evaporating the solvent under reduced pressure to remove any traces of water. The final product was isolated after drying as a solid with melting point 195-197° C. $^1$H NMR (DMSO): 2.55 ppm (3H, s); 2.7 ppm (3H, s); 7.5 ppm (1H, m); 8.3 ppm (1H, m); 8.7 ppm (1H, m); 8.85 ppm (2H, s); 9.15 ppm (1H, m).

Example 4

Preparation of 1-[4-chloro-2-(3-pyridyl)thiazol-5-yl]-N-(4,6-dimethoxypyrimidin-2-yl)oxy-ethanimine (Compound No. 1.058)

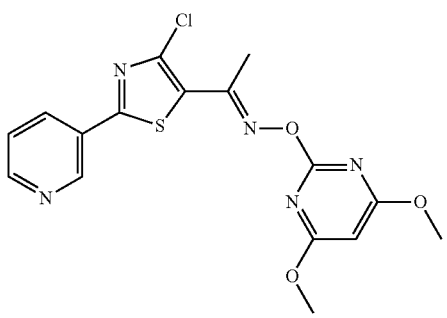

(Compound No. 1.058)

Step a: Preparation of pyridine-3-carbothioamide

Pyridine-3-carbonitrile (10.4 g, 0.1 mol) and $(NH_4)_2S$ (0.1 mol, 34.4 ml, 10 wt. % in $H_2O$) in MeOH (80 ml) was stirred at ambient temperature for 18 hours. The precipated yellow solid was collected by simple filtration and further dried under vacuo to afford pyridine-3-carbothioamide. $^1$H NMR (300 Mz, DMSO-d$^6$): δ 10.06 (br, 1H), 9.69 (br, 1H), 8.96 (d, 1H, J=1.5 Hz), 8.64 (dd, 1H, J=1.8 Hz), 8.18 (m, 1H), 7.44 (m, 1H).

Step b: Preparation of 2-(3-pyridyl)thiazol-4-ol

Pyridine-3-carbothioamide (20 g, 0.145 mol) was dissolved in a mixture of toluene (145 ml) and DMF (116 ml). Ethyl bromoacetate (24.2 g, 0.145 mmol) was added and the reaction mixture was stirred at ambient temperature for 18 hours. The precipitated yellow compound was filtered, washed with water and dried to give 2-(3-pyridyl)thiazol-4-ol as hybromide salt.
$^1$H NMR (300 Mz, DMSO-d$^6$): δ: 9.19 (s, 1H), 8.80 (d, 1H, J=4.5 Hz), 8.62 (d, 1H, J=6.3 Hz), 7.87 (t, 1H, J=5.4 Hz), 6.43 (s, 1H).

Step c: Preparation of 4-chloro-2-(3-pyridyl)thiazole-5-carbaldehyde

Dry DMF (20 ml, 0.255 mol) was cooled to 0-5° C. with an ice/water bath. Phosphorus oxychloride (20 ml, 0.215 mol) was added dropwise over 0.5 h. 2-(3-pyridyl)thiazol-4-ol (hybromide salt, 13 g, 0.05 mol) was added in one portion and the reaction mixture was heated to 110° C. for 15 min. After cooling the reaction mixture was poured on ice water and neutralized with solid potassium carbonate. The precipitate was filtered, washed with water, once with ethanol, and dried to dryness to get 4-chloro-2-(3-pyridyl)thiazole-5-carbaldehyde as brown solid. $^1$H NMR (300 Mz, DMSO-d$^6$): δ: 10.00 (s, 1H), 9.21 (d, 1H, J=1.2 Hz), 8.78 (dd, 1H, J=1.5 Hz), 8.42 (d, 1H, J=7.2 Hz), 7.60 (m, 1H). MS(ESI): 255, 257 (M+MeOH).

Step d: Preparation of 1-[4-chloro-2-(3-pyridyl)thiazol-5-yl]ethanol

4-Chloro-2-(3-pyridyl)thiazole-5-carbaldehyde (1.4 g, 6.25 mmol) was dissolved in dry THF (28 ml) and cooled to –10° C. A 3 M solution of methyl magnesiumchloride in THF (2.08 ml, 6.25 mmol) was added dropwise. The reaction mixture was stirred at ambient temperature for 18 hours. Water (1.7 ml) was added, followed by $CH_3COOH$ (1 ml). The reaction mixture was extracted with ethyl acetate, the organic layer was separated, dried, filtered, and the solvent was evaporated to dryness to get 1-[4-chloro-2-(3-pyridyl)thiazol-5-yl]ethanol as a brown solid. $^1$H NMR (300 Mz, DMSO-d$^6$): δ: 9.07 (s, 1H), 8.68 (dd, 1H, J=1.5 Hz), 8.26 (m, 1H), 7.53 (m, 1H), 5.92 (t, 1H, J=6 Hz), 4.67 (d, 3H, J=5.4 Hz).

Step e: Preparation of 1-[4-chloro-2-(3-pyridyl)thiazol-5-yl]ethanone

1-[4-chloro-2-(3-pyridyl)thiazol-5-yl]ethanol (120 mg, 0.5 mmol) was dissolved in 1,2-dichloroethane (10 ml). Pyridinium chlorochromate (216 mg, 1 mmol) was added to the reaction mixture. The reaction mixture was stirred at 70° C. for 3 hours, cooled to ambient temperature, poured onto a silica gel plug and eluted with dichloromethane. The eluent was evaporated under reduced pressure, and the residue dried to dryness to get 1-[4-chloro-2-(3-pyridyl)thiazol-5-yl]ethanone in form of a white solid. $^1$H NMR (300 Mz, DMSO-d$^6$): δ: 9.17 (s, 1H), 8.75 (d, 1H, J=4.8 Hz), 8.37 (d, 1H, J=8.1 Hz), 7.58 (m, 1H), 2.66 (s, 3H).

Step f: Preparation of 1-[4-chloro-2-(3-pyridyl)thiazol-5-yl]ethanone oxime

To 1-[4-chloro-2-(3-pyridyl)thiazol-5-yl]ethanone (0.5 g, 2.1 mmol) in a mixture of pyridine (2 ml) and methanol (15 ml) was added hydroxylamine hydrochloride (0.29 g, 4.2 mmol). The resluting solution was stirred at ambient temperature for 18 hours. The precipitated white solid was filtered and dried at vacuum to afford the desired 1-[4-chloro-2-(3-pyridyl)thiazol-5-yl]ethanone oxime. $^1$H NMR (300 Mz, DMSO-d$^6$): δ:12.2 (s, 0.29H), 11.89 (s, 0.69H), 9.10 (s, 1H), 8.70 (d, 1H, J=4.8 Hz), 8.30 (m, 1H), 7.55 (m, 1H), 2.41 (s, 1H), 2.29 (s, 2H).

Step g: Preparation of 1-[4-chloro-2-(3-pyridyl)thiazol-5-yl]-N-(4,6-dimethoxypyrimidin-2-yl)oxy-ethanimine (compound 1.058)

To a suspension of sodium hydride (NaH, 60% dispersion in mineral oil: 48 mg, 1.2 mmol) in DMF (2 ml) was added a solution of 1-[4-chloro-2-(3-pyridyl)thiazol-5-yl]ethanone oxime (253.7 mg, 1 mmol) in DMF (3 ml), and the resulting frothy mixture was stirred for 1 hour. After that, 4,6-dimethoxy-2-methylsulfonyl-pyrimidine (218 mg, 1 mmol) was added into the above solution. The homogeneous, dark-red solution was stirred at ambient temperature for 18 hours. The precipitated brown solid was filtered and washed with water and dried under vacuum to afford the brown solid of 1-[4-chloro-2-(3-pyridyl)thiazol-5-yl]-N-(4,6-dimethoxypyrimidin-2-yl)oxy-ethanimine in a mixture of Z and E-isomers. $^1$H NMR (300 Mz, CDCl3): δ: 9.16 (s, 1H), 8.70 (d, 1H, J=4.8 Hz), 8.24 (m, 1H), 7.41 (m, 1H), 5.84 (m, 1H), 3.97 (m, 6H), 2.79 (m, 2H). MS (ESI): 392 (M+1), 414 (M+Na).

Table P: Physical Data of Compounds of Formula I:

In the drawings, free radicals signify an methyl group. A nitro atom at the pyridine ring with free valences (for example compound No. 1.024) represents amino. Therefore, compound No. 1.003

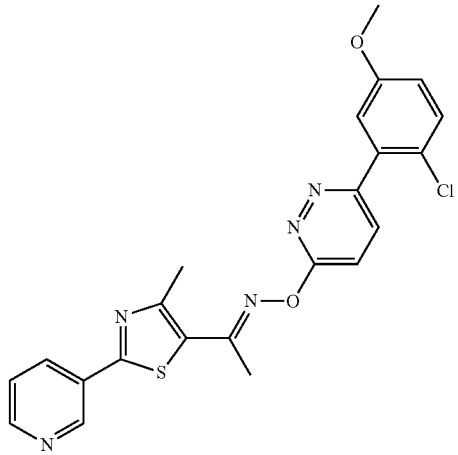
(1.003)

can also be drawn as:

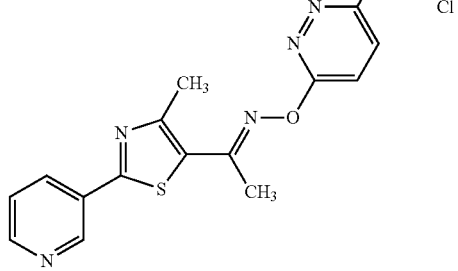
(1.003)

| Compound No. | Structure | Phys. Data |
|---|---|---|
| 1.001 | 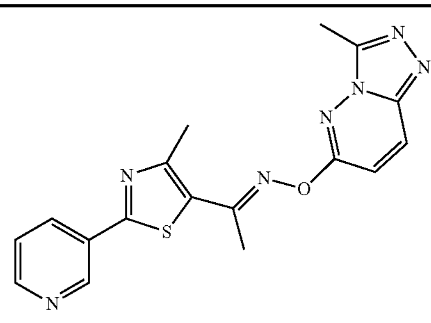 | m.p. 200-202° C. |

-continued

| Compound No. | Structure | Phys. Data |
|---|---|---|
| 1.002 | 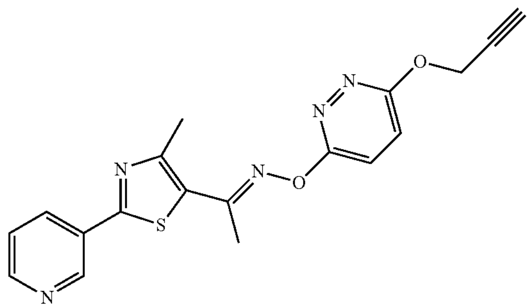 [SMILES: C#CCOc1ccc(O/N=C(\C)c2sc(-c3cccnc3)nc2C)nn1] | m.p. 152-154° C. |
| 1.003 | 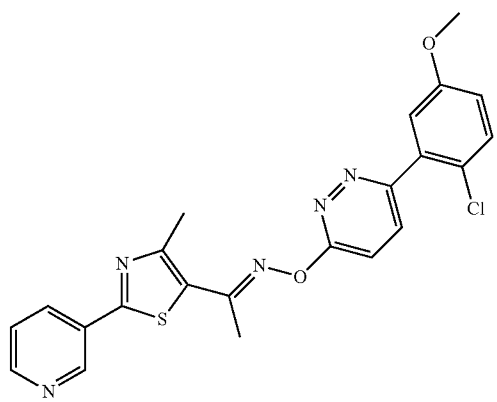 [SMILES: COc1ccc(Cl)c(-c2ccc(O/N=C(\C)c3sc(-c4cccnc4)nc3C)nn2)c1] | m.p. 169-171° C. |
| 1.004 | 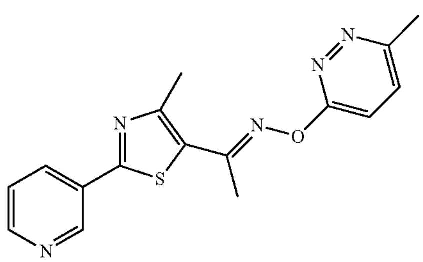 [SMILES: C/C(=N\Oc1ccc(C)nn1)c1sc(-c2cccnc2)nc1C] | m.p. 179-181° C. |
| 1.005 | 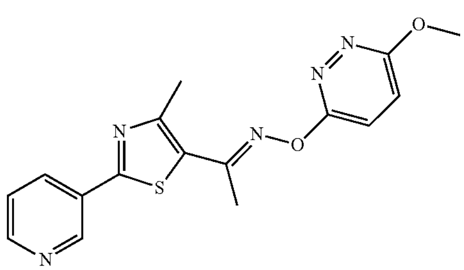 [SMILES: COc1ccc(O/N=C(\C)c2sc(-c3cccnc3)nc2C)nn1] | m.p. 167-169° C. |
| 1.006 | 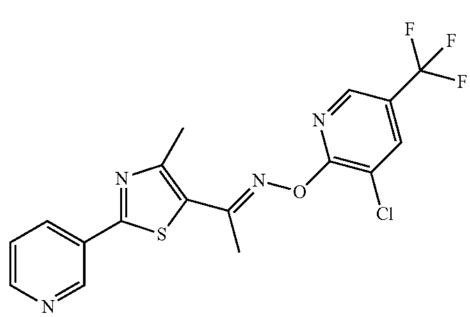 [SMILES: C/C(=N\Oc1ncc(C(F)(F)F)cc1Cl)c1sc(-c2cccnc2)nc1C] | LCMS: 414 (M + 1) |

-continued

| Compound No. | Structure | Phys. Data |
|---|---|---|
| 1.007 | 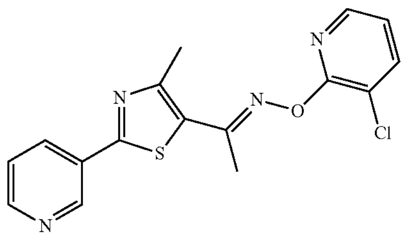 [SMILES: C/C(=N\Oc1ncccc1Cl)c1sc(-c2cccnc2)nc1C] | m.p. 126-128° C. |
| 1.008 | 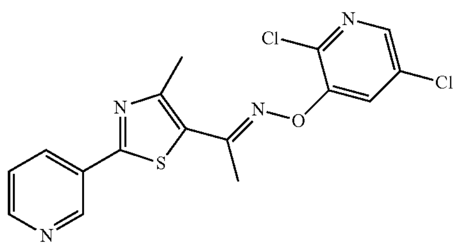 [SMILES: C/C(=N\Oc1cc(Cl)cnc1Cl)c1sc(-c2cccnc2)nc1C] | m.p. 161-162° C. |
| 1.009 | 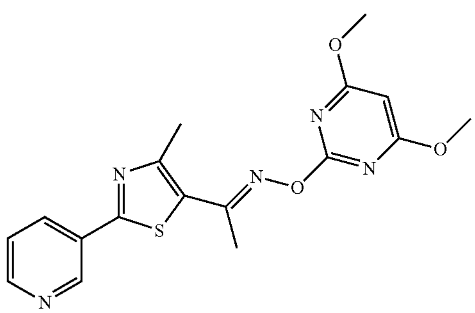 [SMILES: COc1cc(OC)nc(O/N=C(\C)c2sc(-c3cccnc3)nc2C)n1] | m.p. 164-165° C. |
| 1.010 | 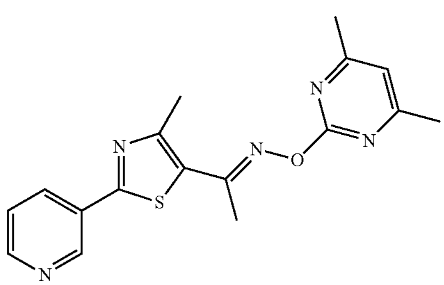 [SMILES: C/C(=N\Oc1nc(C)cc(C)n1)c1sc(-c2cccnc2)nc1C] | m.p. 162-163° C. |
| 1.011 | 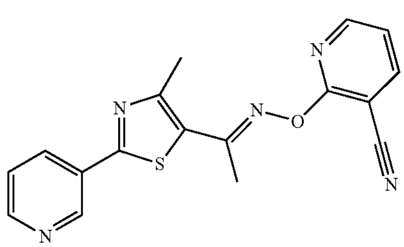 [SMILES: C/C(=N\Oc1ncccc1C#N)c1sc(-c2cccnc2)nc1C] | m.p. 179-180° C. |

-continued

| Compound No. | Structure | Phys. Data |
|---|---|---|
| 1.012 | 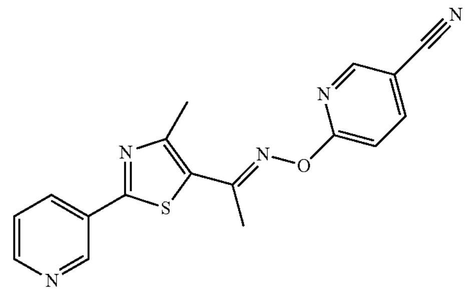 [SMILES: C/C(=N\Oc1ccc(C#N)cn1)c1sc(-c2cccnc2)nc1C] | m.p. 197-198° C. |
| 1.013 | 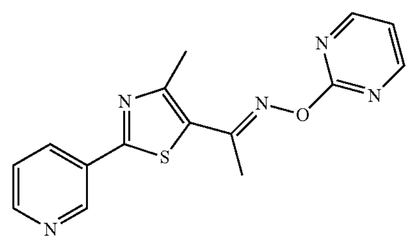 [SMILES: C/C(=N\Oc1ncccn1)c1sc(-c2cccnc2)nc1C] | m.p. 122-123° C. |
| 1.014 | 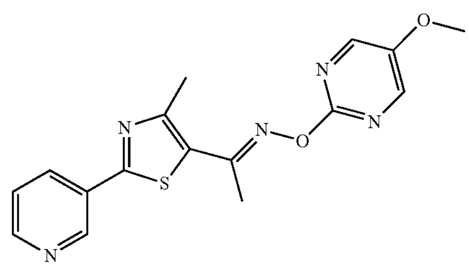 [SMILES: COc1cnc(O/N=C(\C)c2sc(-c3cccnc3)nc2C)nc1] | m.p. 145-147° C. |
| 1.015 | 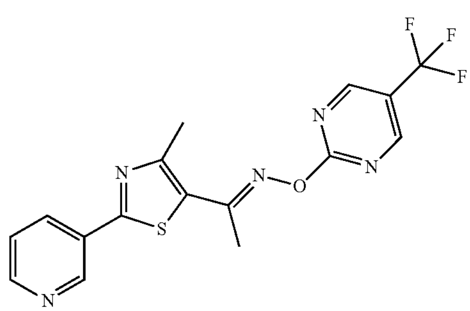 [SMILES: C/C(=N\Oc1ncc(C(F)(F)F)cn1)c1sc(-c2cccnc2)nc1C] | m.p. 165-166° C. |
| 1.016 | 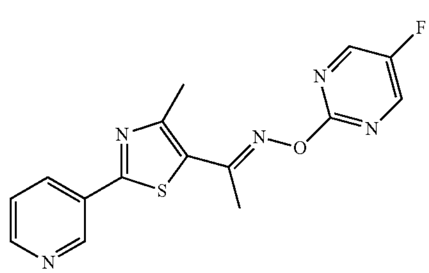 [SMILES: C/C(=N\Oc1ncc(F)cn1)c1sc(-c2cccnc2)nc1C] | m.p. 161-163° C. |

-continued

| Compound No. | Structure | Phys. Data |
|---|---|---|
| 1.017 | 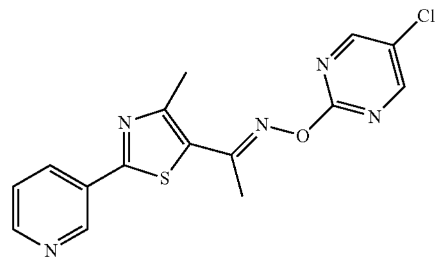 [SMILES: C/C(=N\Oc1ncc(Cl)cn1)c1sc(-c2cccnc2)nc1C] | m.p. 195-197° C. |
| 1.018 | 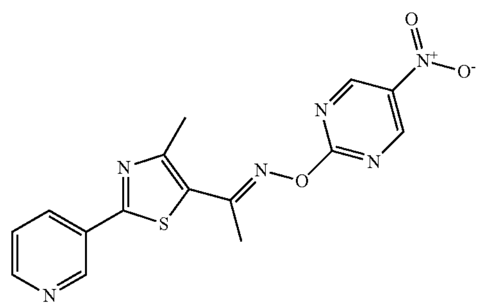 [SMILES: C/C(=N\Oc1ncc([N+](=O)[O-])cn1)c1sc(-c2cccnc2)nc1C] | m.p. 174-176° C. |
| 1.019 | 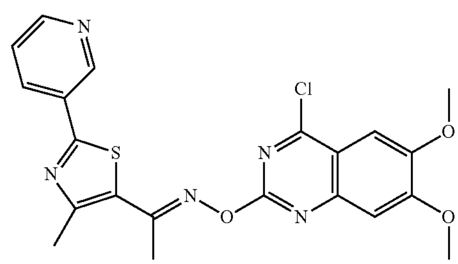 [SMILES: COc1cc2nc(O/N=C(\C)c3sc(-c4cccnc4)nc3C)nc(Cl)c2cc1OC] | LCMS: 455 (M + 1) |
| 1.020 | 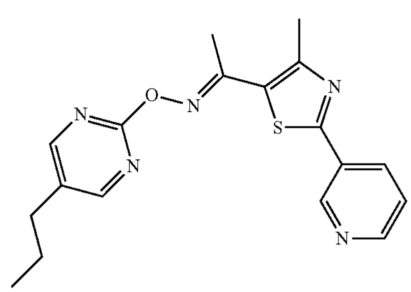 [SMILES: CCCc1cnc(O/N=C(\C)c2sc(-c3cccnc3)nc2C)nc1] | LCMS: 353 (M + 1) |
| 1.021 | 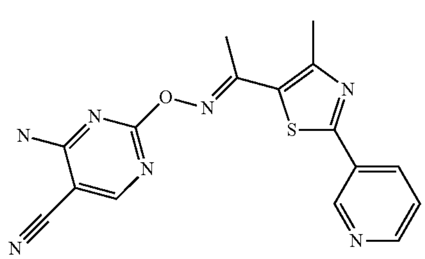 [SMILES: C/C(=N\Oc1ncc(C#N)c(N)n1)c1sc(-c2cccnc2)nc1C] | LCMS: 351 (M + 1) |

-continued

| Compound No. | Structure | Phys. Data |
|---|---|---|
| 1.022 | 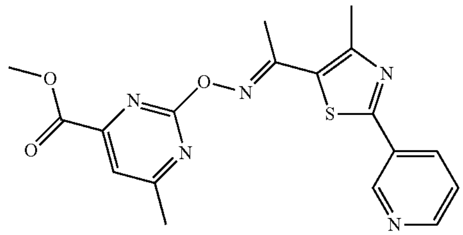 [SMILES: COC(=O)c1cc(C)nc(O/N=C(\C)c2sc(-c3cccnc3)nc2C)n1] | LCMS: 383 (M + 1) |
| 1.023 | 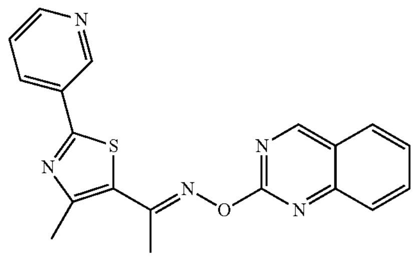 [SMILES: C/C(=N\Oc1ncc2ccccc2n1)c1sc(-c2cccnc2)nc1C] | LCMS: 362 (M + 1) |
| 1.024 | 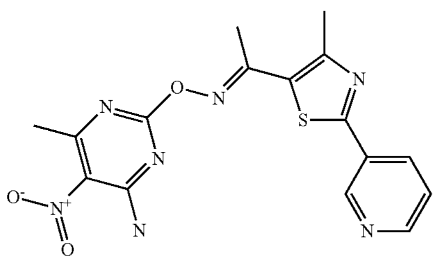 [SMILES: C/C(=N\Oc1nc(C)c([N+](=O)[O-])c(N)n1)c1sc(-c2cccnc2)nc1C] | LCMS: 386 (M + 1) |
| 1.025 | 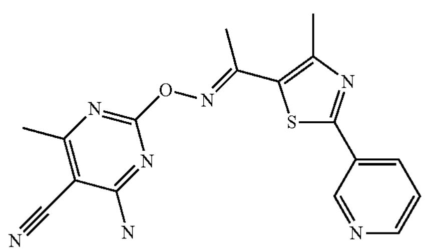 [SMILES: C/C(=N\Oc1nc(C)c(C#N)c(N)n1)c1sc(-c2cccnc2)nc1C] | LCMS: 366 (M + 1) |
| 1.026 | 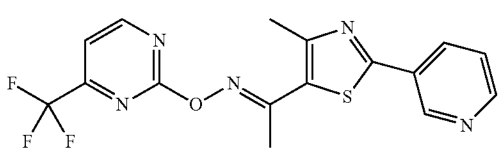 [SMILES: C/C(=N\Oc1nccc(C(F)(F)F)n1)c1sc(-c2cccnc2)nc1C] | LCMS: 380 (M + 1) |
| 1.027 | 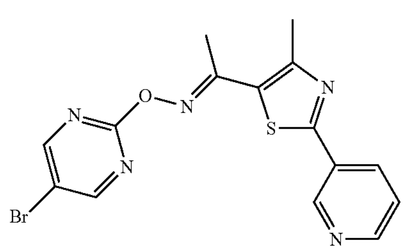 [SMILES: C/C(=N\Oc1ncc(Br)cn1)c1sc(-c2cccnc2)nc1C] | LCMS: 390 (M + 1) |

-continued

| Compound No. | Structure | Phys. Data |
|---|---|---|
| 1.028 | 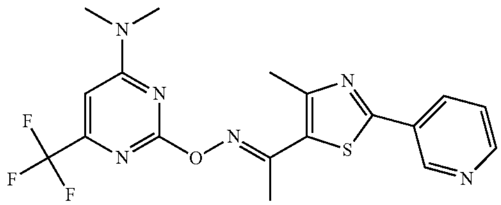 [SMILES: C/C(=N\Oc1nc(N(C)C)cc(C(F)(F)F)n1)c1sc(-c2cccnc2)nc1C] | LCMS: 423 (M + 1) |
| 1.029 | 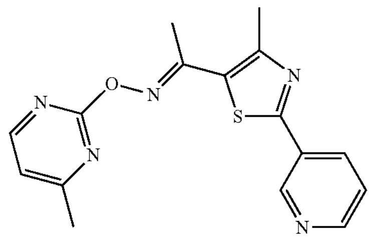 [SMILES: C/C(=N\Oc1nccc(C)n1)c1sc(-c2cccnc2)nc1C] | LCMS: 326 (M + 1) |
| 1.030 | 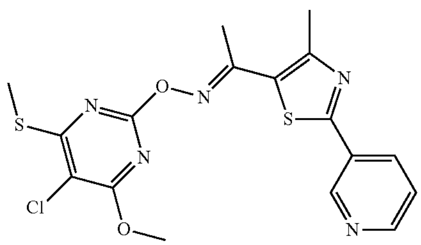 [SMILES: COc1nc(O/N=C(\C)c2sc(-c3cccnc3)nc2C)nc(SC)c1Cl] | LCMS: 422 (M + 1) |
| 1.031 | 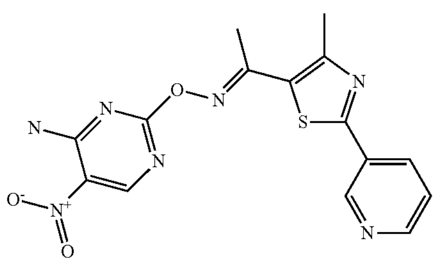 [SMILES: C/C(=N\Oc1ncc([N+](=O)[O-])c(N)n1)c1sc(-c2cccnc2)nc1C] | LCMS: 372 (M + 1) |
| 1.032 | 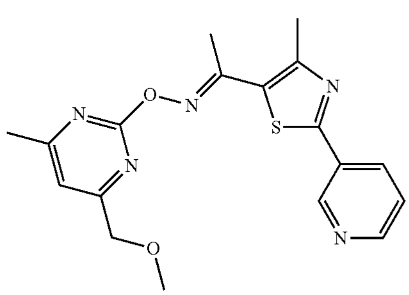 [SMILES: COCc1cc(C)nc(O/N=C(\C)c2sc(-c3cccnc3)nc2C)n1] | LCMS: 370 (M + 1) |
| 1.033 | 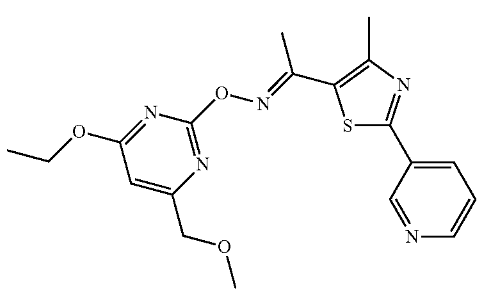 [SMILES: CCOc1cc(COC)nc(O/N=C(\C)c2sc(-c3cccnc3)nc2C)n1] | LCMS: 400 (M + 1) |

-continued

| Compound No. | Structure | Phys. Data |
|---|---|---|
| 1.034 | 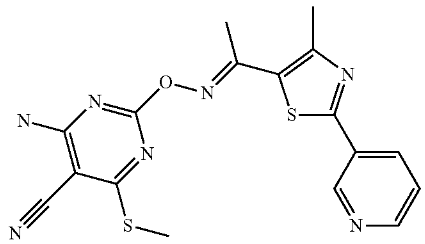 [SMILES: CSc1nc(O/N=C(\C)c2sc(-c3cccnc3)nc2C)nc(N)c1C#N] | LCMS: 398 (M + 1) |
| 1.035 | 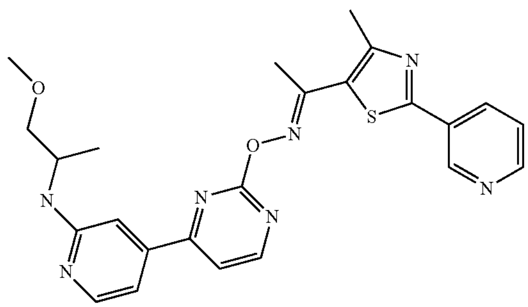 [SMILES: COCC(C)Nc1cc(-c2ccnc(O/N=C(\C)c3sc(-c4cccnc4)nc3C)n2)ccn1] | LCMS: 476 (M + 1) |
| 1.036 | 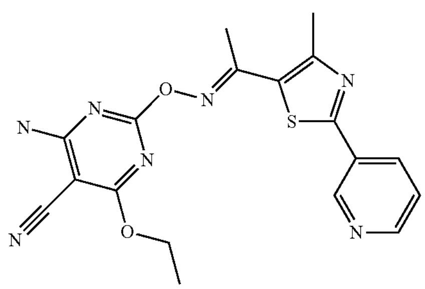 [SMILES: CCOc1nc(O/N=C(\C)c2sc(-c3cccnc3)nc2C)nc(N)c1C#N] | LCMS: 395 (M + 1) |
| 1.037 | 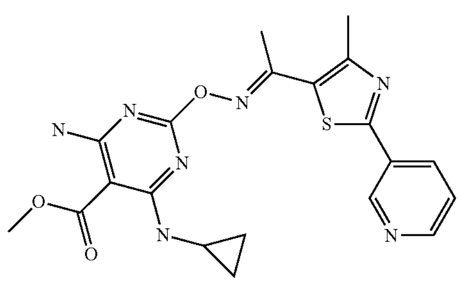 [SMILES: COC(=O)c1c(N)nc(O/N=C(\C)c2sc(-c3cccnc3)nc2C)nc1NC1CC1] | LCMS: 440 (M + 1) |
| 1.038 | 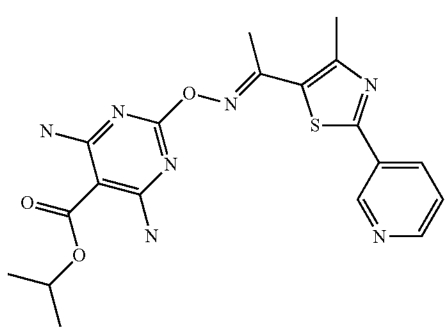 [SMILES: C/C(=N\Oc1nc(N)c(C(=O)OC(C)C)c(N)n1)c1sc(-c2cccnc2)nc1C] | LCMS: 428 (M + 1) |

-continued

| Compound No. | Structure | Phys. Data |
|---|---|---|
| 1.039 | 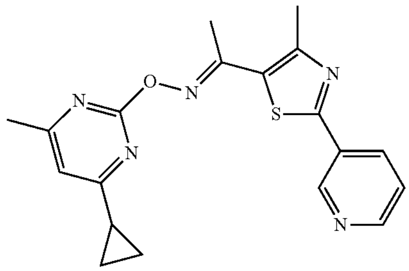 [SMILES: C/C(=N\Oc1nc(C)cc(C2CC2)n1)c1sc(-c2cccnc2)nc1C] | LCMS: 366 (M + 1) |
| 1.040 | 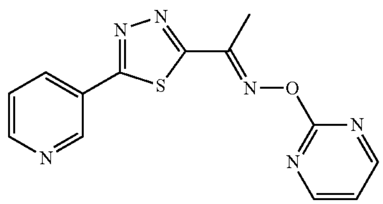 [SMILES: C/C(=N\Oc1ncccn1)c1nnc(-c2cccnc2)s1] | LCMS: 299 (M + 1) |
| 1.041A | Isomer A | LCMS: 298 (M + 1) |
| 1.041B | Isomer B | LCMS: 298 (M + 1) |
| 1.042 | 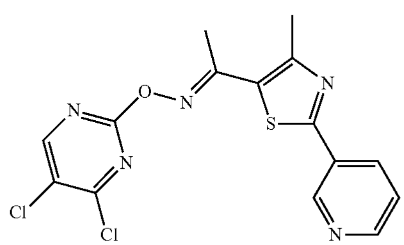 [SMILES: C/C(=N\Oc1ncc(Cl)c(Cl)n1)c1sc(-c2cccnc2)nc1C] | LCMS: 380 (M + 1) |
| 1.043 | 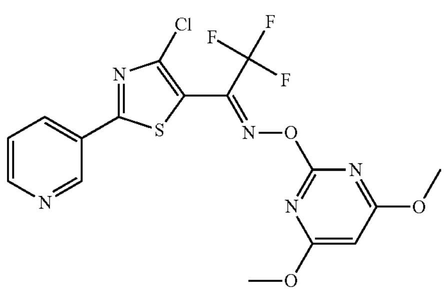 [SMILES: COc1cc(OC)nc(O/N=C(/c2sc(-c3cccnc3)nc2Cl)C(F)(F)F)n1] | m.p. 109-111° C. |

-continued
| Compound No. | Structure | Phys. Data |
|---|---|---|
| 1.044 | 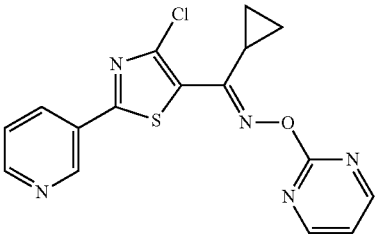 [SMILES: Clc1nc(-c2cccnc2)sc1/C(=N/Oc1ncccn1)C1CC1] | m.p. 127-130° C. |
| 1.045 | 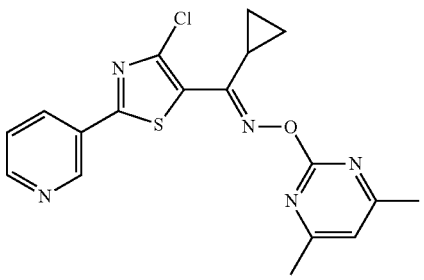 [SMILES: Cc1cc(C)nc(O/N=C(/c2sc(-c3cccnc3)nc2Cl)C2CC2)n1] | m.p. 53-55° C. |
| 1.046 | 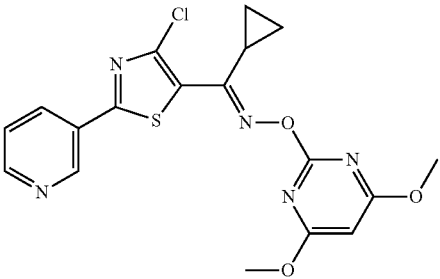 [SMILES: COc1cc(OC)nc(O/N=C(/c2sc(-c3cccnc3)nc2Cl)C2CC2)n1] | m.p. 54-56° C. |
| 1.047 | 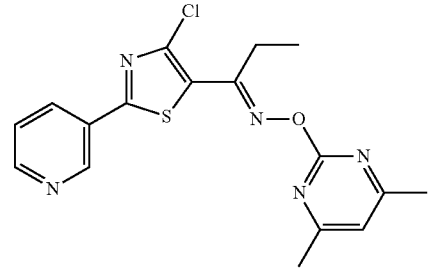 [SMILES: CC/C(=N\Oc1nc(C)cc(C)n1)c1sc(-c2cccnc2)nc1Cl] | m.p. 89-94° C. |
| 1.048 | 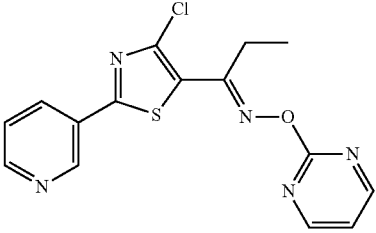 [SMILES: CC/C(=N\Oc1ncccn1)c1sc(-c2cccnc2)nc1Cl] | ESI-MS (+): 368 (M + Na)+ |

-continued

| Compound No. | Structure | Phys. Data |
|---|---|---|
| 1.049 | 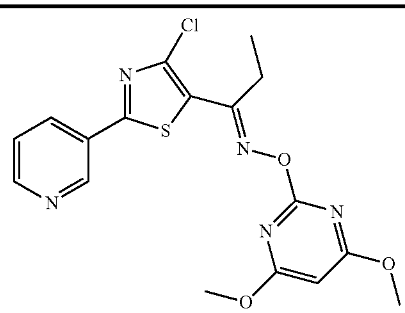 | m.p. 120-124° C. |
| 1.050 | 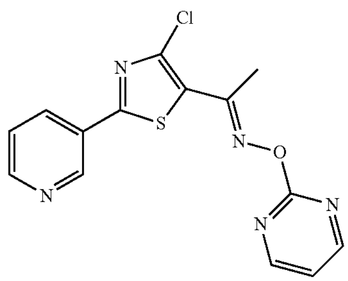 [SMILES: C/C(=N\Oc1ncccn1)c1sc(-c2cccnc2)nc1Cl] | m.p. 198-200° C. |
| 1.051 | 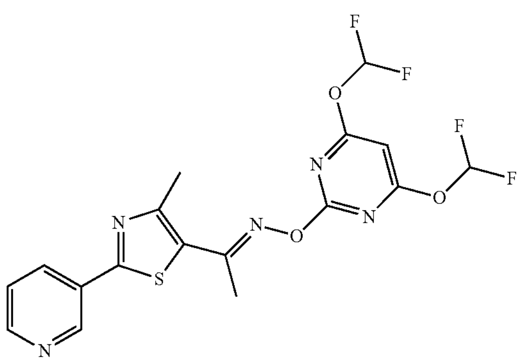 [SMILES: C/C(=N\Oc1nc(OC(F)F)cc(OC(F)F)n1)c1sc(-c2cccnc2)nc1C] | LCMS: 444 (M + 1) |
| 1.052 | 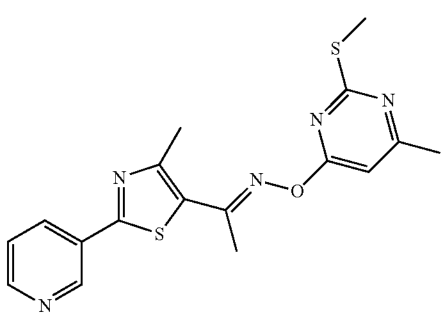 [SMILES: CSc1nc(C)cc(O/N=C(\C)c2sc(-c3cccnc3)nc2C)n1] | LCMS: 372 (M + 1) |
| 1.053 | 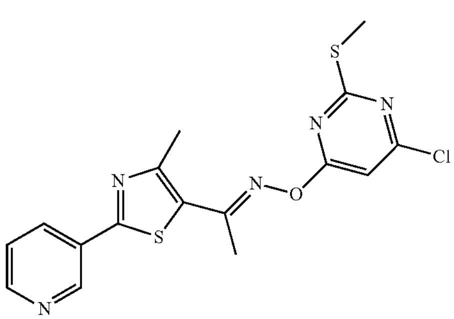 [SMILES: CSc1nc(Cl)cc(O/N=C(\C)c2sc(-c3cccnc3)nc2C)n1] | LCMS: 393 (M + 1) |

-continued

| Compound No. | Structure | Phys. Data |
|---|---|---|
| 1.054 | 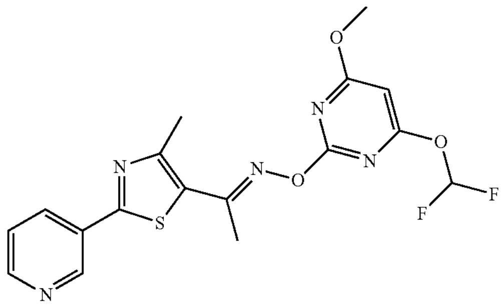 [SMILES: COc1cc(OC(F)F)nc(O/N=C(\C)c2sc(-c3cccnc3)nc2C)n1] | LCMS: 408 (M + 1) |
| 1.055 | 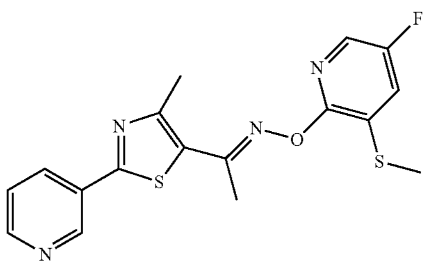 [SMILES: CSc1cc(F)cnc1O/N=C(\C)c1sc(-c2cccnc2)nc1C] | m.p. 149-151° C. |
| 1.056 | 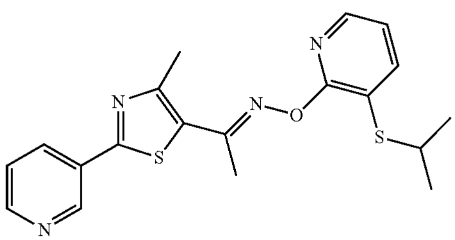 [SMILES: C/C(=N\Oc1ncccc1SC(C)C)c1sc(-c2cccnc2)nc1C] | LCMS: 385 (M + 1) |
| 1.057 | 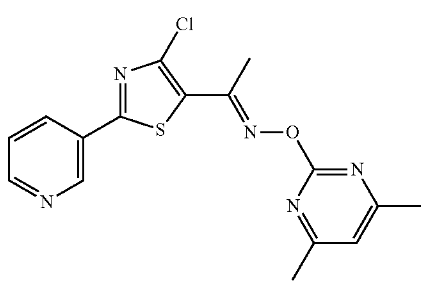 [SMILES: C/C(=N\Oc1nc(C)cc(C)n1)c1sc(-c2cccnc2)nc1Cl] | m.p. 157-160° C. |
| 1.058 | 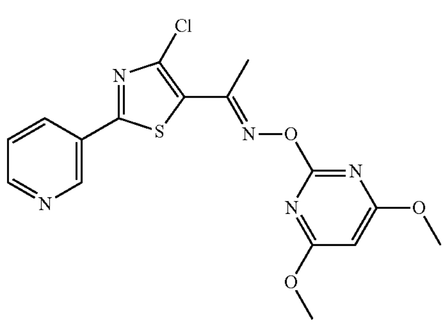 [SMILES: COc1cc(OC)nc(O/N=C(\C)c2sc(-c3cccnc3)nc2Cl)n1] | m.p. 133-136° C. |

-continued

| Compound No. | Structure | Phys. Data |
|---|---|---|
| 1.059 | 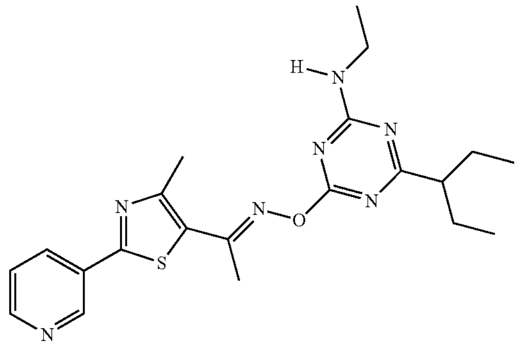 [SMILES: CCNc1nc(O/N=C(\C)c2sc(-c3cccnc3)nc2C)nc(C(CC)CC)n1] | LCMS: 427 (M + 1) |
| 1.060 | 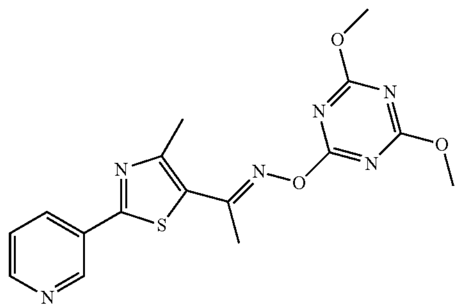 [SMILES: COc1nc(OC)nc(O/N=C(\C)c2sc(-c3cccnc3)nc2C)n1] | m.p. 171-173° C. |
| 1.061 | 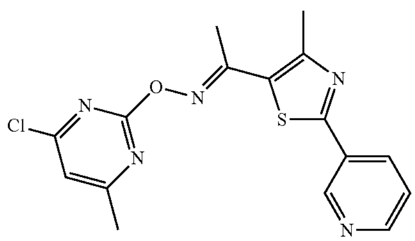 [SMILES: C/C(=N\Oc1nc(C)cc(Cl)n1)c1sc(-c2cccnc2)nc1C] | LCMS: 360 (M + 1) |
| 1.062 | 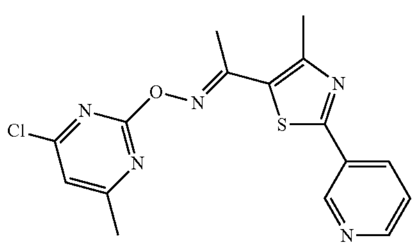 [SMILES: C/C(=N\Oc1nc(C)cc(Cl)n1)c1sc(-c2cccnc2)nc1C] | LCMS: 359 (M + 1) |
| 1.063 | 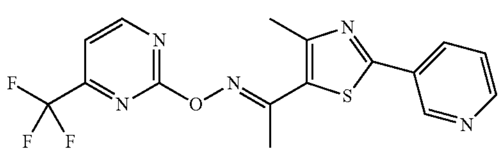 [SMILES: C/C(=N\Oc1nccc(C(F)(F)F)n1)c1sc(-c2cccnc2)nc1C] | LCMS: 379 (M + 1) |

LCMS Method:
LCMS:
LCMS. Spectra were recorded on a ACQUITY SQD Mass Spectrometer (Waters Corp. Milford, Mass., USA) mass spectrometer equipped with an electrospray source (ESI; source temperature 150° C.; desolvation temperature 400° C.; cone voltage 20 V; cone gas flow 60 l/hour, desolvation gas flow 700 l/hour, mass range: 100 to 800 Da) and a Waters ACQUITY UPLC (column: Waters ACQUITY UPLC HSS T3, 30 mm, Internal diameter of column: 2.1 mm; Particle Size: 1.8 micron; column temperature: 60° C.; flow rate 0.75 ml/min; eluent A: Water/Methanol 9:1, 0.1% formic acid;

eluent B: Acetonitrile, 0.1°/0 formic acid; gradient: 0 min 5% B; 2-2.8 (6-7.7) min 100% B; 2.9-3 (7.8-8) min 5% B; UV-detection: 210-500 nm, resolution 2 nm. The flow was split postcolumn prior to MS analysis.

ESI-MS:

MS: Instrument model: Shimadzu LCMS-2010EV; ESI (+)/ESI (−) scan mode; Nebulizer gas: 1.5 ml/min; CDL temperature: 250° C.; Interface Voltage: 3.5 kV; Detector Voltage: 1.5 kV.

HPLC: Instrument model: Shimadzu LC-20AD; UV wavelength: 254 nm; Flow rate: 0.2 ml/min; Column temperature: 40° C.; Mobile phase: Methanol/water=4:1; Column condition: Inertsil ODS-SP C18, 4.6×150 mm, 5 □nm; Gradient elution:

|  | Time (min) | | |
| --- | --- | --- | --- |
|  | 0 | 15 | 25 |
| Acetonitrile % | 10 | 100 | 100 |

The compounds according to the following tables can be prepared analogously. The examples which follow are intended to illustrate the invention and show preferred compounds of formula I.

Formulation Examples

%=Percent by Weight

| Example F1: Emulsion concentrates | a) | b) | c) |
| --- | --- | --- | --- |
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
| --- | --- | --- | --- | --- |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
| --- | --- | --- | --- | --- |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
| --- | --- | --- |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
| --- | --- | --- | --- |
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
| --- | --- |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
| --- | --- |
| Polyethylene glycol (MW 200) | 3% |
| Kaolin | 94% |

In a mixer, the finely ground active ingredient is applied uniformLy to the kaolin, which has been moistened with the polyethylene glycol. This gives dust-free coated granules.

Example F8

Suspension Concentrate

| Active ingredient | 40% |
| --- | --- |
| Ethylene glycol | 10% |
| Nonylphenoxypolyethylene glycol ether (15 mol of EO) | 6% |
| Sodium lignosulfonate | 10% |
| Carboxymethylcellulose | 1% |

-continued

| | |
|---|---|
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds of formulae 1.001 to 1.063 described in Tables P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and yl-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347)

and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl)ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl 0-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+

TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene Ill (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, teral-lethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, yl-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+

TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-5-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [522]-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731]-27-1]+

TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [1,3]-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-5-methyl [135158-54-2]+TX, anilazine [10]-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, 1-[4-[4-[5S)-5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX and 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone ([CAS-RNr.: 1003318-67-9], both disclosed in WO 2010/123791, WO 2008/013925, WO 2008/013622 and WO 2011/051243 page 20)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from table P with active ingredients described above comprises a compound selected from table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from table P and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Biological Examples

%=Percent by Weight, Unless Otherwise Specified

Example B1

Activity Against *Spodoptera littoralis* (Egyptian Cotton Leafworm)

(Larvicide, Feeding/Residual Contact Activity, Preventive)

Cotton leaf discs were placed on agar in a 24-well microtiter plate and sprayed with test solutions. After drying, the leaf discs were infested with 5 $L_1$ larvae. The samples were checked for mortality, repellent effect, feeding behaviour, and growth regulation 3 days after treatment.

In this test, compounds 1.008 and 1.042 showed an activity of over 80% at a concentration of 200 ppm.

Example B2

*Plutella xylostella* (Diamond Back Moth)

(Larvicide, Feeding/Residual Contact Activity, Preventive)

24-well microtiter plate (MTP) with artificial diet was treated with test solutions by pipetting. After drying, the MTP's were infested with larvae (L2)(10-15 per well). After an incubation period of 5 days, samples were checked for larval mortality, antifeedant and growth regulation.

In this test, compound 1.012 showed an activity of over 80% at a concentration of 200 ppm.

Example B3

Activity against *Myzus persicae* (Green Peach Aphid)

(Mixed Population, Feeding/Residual Contact Activity, Preventive)

Sunflower leaf discs were placed on agar in a 24-well microtiter plate and sprayed with test solutions. After drying, the leaf discs were infested with an aphid population of mixed ages. After an incubation period of 6 days, samples were checked for mortality. In this test, compounds 1.008, 1.009, 1.010, 1.013 1.014, 1.020, 1.029, 1.032, 1.041, 1.047, 1.048, 1.049, 1.050, 1.056, 51.07, 1.058, and 1.060 showed an activity of over 80% at a concentration of 200 ppm.

Example B4

Activity Against *Tetranychus urticae* (Two-Spotted Spider Mite)

(Mixed Population, Feeding/Contact Activity, Preventive)

Bean leaf discs on agar in 24-well microtiter plates were sprayed with test solutions. After drying, the leaf discs were infested with mite populations of mixed ages. 8 days later, discs were checked for egg mortality, larval mortality, and adult mortality. In this test, compounds 1.008 and 1.011 showed an activity of over 80% at a concentration of 200 ppm.

Example B5

Activity Against *Bemisia tabaci* (Cotton White Fly)

(Feeding/Residual Contact Activity, Preventive)

Cotton leaf discs were placed on agar in a 24-well microtiter plate and sprayed with test solutions. After drying, the leaf discs were infested with 12 to 18 adults. After an incubation period of 6 days after infestation, samples were checked for mortality and special effects (e.g. phytotoxicity). In this test, compound 1.014, 1.016, 1.041, 1.046, 1.053 and 1.057 showed an activity of over 80% at a concentration of 200 ppm.

What is claimed is:

1. A compound of formula I

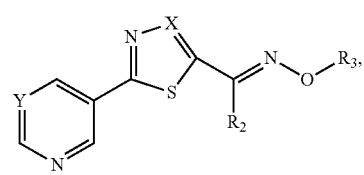

(I)

wherein
X is nitrogen or C—$R_1$;
Y is nitrogen or C—$R_4$;
$R_1$ is hydrogen, $C_1$-$C_6$alkyl or halogen;
$R_2$ is $C_1$-$C_6$alkyl which is optionally mono- to polysubstituted by substituents independently selected from the group consisting of halogen, nitro, cyano, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or $R_2$ is $C_3$-$C_6$cycloalkyl which is optionally mono- to polysubstituted by substituents independently selected from the group consisting of halogen, nitro, cyano, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl;

$R_3$ is a five- to ten-membered monocyclic or fused bicyclic ring system which is optionally aromatic, partially saturated or fully saturated and can contain 1 to 4 hetero atoms selected from the group consisting of nitrogen, oxygen and sulfur, each ring system does not contain more than 2 oxygen atoms and more than 2 sulfur atoms, and the five- to ten-membered ring system itself is optionally mono- to polysubstituted by substituents independently selected from the group consisting of halogen, cyano, nitro, amino, hydroxy, $C_1$-$C_6$alkyl, $C_2$-$C_6$alkenyl, $C_2$-$C_6$alkynyl, $C_2$-$C_6$alkynyloxy, $C_3$-$C_6$cycloalkyl, $C_5$-$C_7$cycloalkenyl, $C_5$-$C_8$cycloalkynyl, $C_3$-$C_6$cycloalkylamino, $C_1$-$C_6$haloalkyl, $C_2$-$C_6$haloalkenyl, $C_2$-$C_6$haloalkynyl, $C_3$-$C_6$halocycloalkyl, $C_2$-$C_7$halocycloalkenyl, $C_2$-$C_8$halocycloalkynyl, $C_1$-$C_6$alkoxy-$C_1$-$C_6$alkylamino, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$alkylamino, di-($C_1$-$C_6$alkyl)amino, $C_3$-$C_6$cycloalkylamino, $C_1$-$C_6$alkyl-$C_3$-$C_6$cycloalkylamino, $C_1$-$C_6$alkylcarbonyl, $C_1$-$C_6$alkoxycarbonyl, $C_1$-$C_6$alkylaminocarbonyl, $C_1$-$C_6$dialkylaminocarbonyl, $C_1$-$C_6$alkoxycarbonyloxy, $C_1$-$C_6$alkylaminocarbonyloxy, $C_1$-$C_6$dialkylaminocarbonyloxy, tri-($C_1$-$C_6$alkyl)silyl or phenyl, where the phenyl group is optionally mono- to polysubstituted by substituents independently selected from the group consisting of hydroxy, $C_1$-$C_6$alkyl, $C_1$-$C_6$haloalkyl, $C_1$-$C_6$alkoxy, $C_1$-$C_6$alkylthio, $C_1$-$C_6$haloalkylthio, $C_2$-$C_6$alkenylthio, $C_2$-$C_6$haloalkenylthio, $C_2$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di-($C_1$-$C_2$alkyl)aminosulfonyl, di($C_1$-$C_4$alkyl)amino, halogen, cyano and nitro; and the substituents at the nitrogen atoms in the ring systems being other than halogen; and $R_4$ is hydrogen or halogen;

and agrochemically acceptable salts, enantiomers, tautomers and N-oxides of those compounds.

2. A compound of formula I according to claim 1, wherein said ring system $R_3$ is aromatic.

3. A compound of formula I according to claim 2, wherein $R_3$ is mono- to polysubstituted by substituents selected from the group consisting of $C_1$-$C_6$alkyl, $C_1$-$C_6$haloalkyl, $C_1$-$C_6$alkylthio, $C_1$-$C_6$alkoxy, $C_1$-$C_6$alkoxy-$C_1$-$C_6$alkylamino, $C_1$-$C_6$alkoxycarbonyl, $C_2$-$C_6$alkynyloxy, $C_3$-$C_6$cycloalkyl, halogen, cyano, nitro, amino, di-($C_1$-$C_6$alkyl)amino, $C_3$-$C_6$cycloalkylamino and phenyl, where the phenyl group is optionally mono- to polysubstituted by substituents independently selected from the group consisting of halogen and $C_1$-$C_6$alkoxy.

4. A compound of formula I according to claim 2, wherein the ring system $R_3$ is a six-membered aromatic ring system containing 2 nitrogen atoms.

5. A compound of formula I according to claim 2, wherein said ring system $R_3$ is selected from the group consisting of [1,2,4]triazolo[4,3-b]pyridazinyl, pyridazinyl, pyridyl, pyrimidinyl and quinazolinyl.

6. A compound of formula I according to claim 2, wherein the ring system $R_3$ is 2-pyrimidyl.

7. A compound of formula I according to claim 1, wherein $R_2$ is $C_1$-$C_6$alkyl which is optionally mono- to disubstituted by substituents independently selected from the group consisting of halogen, nitro, cyano, $C_1$-$C_6$alkoxy, $C_1$-$C_6$alkylthio, $C_1$-$C_6$alkylsulfinyl and $C_1$-$C_6$alkylsulfonyl.

8. A compound of formula I according to claim 1, wherein $R_1$ is $C_1$-$C_6$alkyl or halogen; and $R_2$ is $C_1$-$C_6$alkyl.

9. A compound of formula I according to claim 1, wherein $R_1$ is methyl or chloro; and $R_2$ is methyl.

10. A compound of formula I according to claim 1, wherein $R_4$ is hydrogen or fluorine.

11. A pesticidal composition, which comprises at least one compound of formula I according to claim 1 or, a tautomer thereof, in free form or in agrochemically utilizable salt form, as active ingredient and at least one auxiliary.

12. A composition according to claim 11 for controlling insects or representatives of the order Acarina.

13. A method for controlling pests, which comprises applying a composition according to claim 11 to pests or to an environment of the pests with the exception of a method for treatment of a human or an animal body by surgery or therapy and diagnostic methods practised on the human or animal body.

14. A method for protection of plant propagation material from attack by pests, which comprises treating the propagation material or a site where the propagation material is planted with a composition according to claim 11.

15. Plant propagation material treated in accordance with the method described in claim 14.

* * * * *